(12) United States Patent
Carlucci

(10) Patent No.: US 9,730,758 B2
(45) Date of Patent: Aug. 15, 2017

(54) SKIN TREATMENT APPARATUS

(71) Applicant: Conair Corporation, Stamford, CT (US)

(72) Inventor: Vito James Carlucci, Stratford, CT (US)

(73) Assignee: Conair Corporation, Stamford ( * ) Notice: Subject to any disclaimer, the term of this patent is extended or adjusted under 35 U.S.C. 154(b) by 71 days.

(21) Appl. No.: 14/133,988

(22) Filed: Dec. 19, 2013

(65) Prior Publication Data

US 2015/0173842 A1  Jun. 25, 2015

(51) Int. Cl.
| | |
|---|---|
| A61B 17/50 | (2006.01) |
| A61B 19/00 | (2006.01) |
| A46B 15/00 | (2006.01) |
| A61H 7/00 | (2006.01) |
| A61H 23/02 | (2006.01) |

(Continued)

(52) U.S. Cl.
CPC ............ *A61B 19/36* (2013.01); *A46B 13/008* (2013.01); *A46B 13/023* (2013.01); *A46B 15/0006* (2013.01); *A46B 15/0008* (2013.01); *A61B 90/80* (2016.02); *A61H 7/005* (2013.01); *A61H 23/02* (2013.01); *A46B 2200/102* (2013.01); *A61H 2201/1671* (2013.01); *A61H 2201/1676* (2013.01); *A61H 2201/5043* (2013.01); *A61H 2205/022* (2013.01)

(58) Field of Classification Search
CPC A61B 2017/00747; A61B 2017/00761; A61B 19/36; A61B 2017/00752; A61B 2017/00756; A61B 2017/00769; A61B 2017/00774; A61B 2017/00792; A61B 34/25; A61B 2034/252; A61B 2034/254; A61B 2034/256; A61B 2034/258; A61N 1/328; A61H 2201/5023; A61H 2201/5025; A61H 2201/5028; A61H 2201/503; A61H 2201/5033; A61H 2201/5035; A61H 2201/5038; A61H 2201/5041; A61H 2201/5043; A61H 2201/5046; A61H 2201/5048
USPC ......................................................... 606/131
See application file for complete search history.

(56) References Cited

U.S. PATENT DOCUMENTS

| | | |
|---|---|---|
| 5,891,063 A | 4/1999 | Vigil |
| D452,044 S | 12/2001 | Goetschi |

(Continued)

OTHER PUBLICATIONS

International Search Report for corresponding PCT application No. PCT/US14/1167, dated Mar. 11, 2015, 6 pages.

*Primary Examiner* — Jonathan Miles
*Assistant Examiner* — Kankindi Rwego
(74) *Attorney, Agent, or Firm* — Lawrence Cruz; Joseph W. Schmidt, P.C.

(57) ABSTRACT

A facial treatment apparatus includes a housing, a facial treatment member mounted to the housing, and dimensioned for application to facial skin of a subject and being actuable to treat the facial skin, a visual display including a facial icon having a plurality of regions corresponding to different areas of the facial skin to be treated by the facial treatment member, an electronic timer adapted to count time associated with a treatment protocol and responsive to actuation of the facial treatment member and a controller associated with the timer and the facial icon and cooperating to visually identify a different region of the facial icon at successive predetermined time intervals of the treatment protocol.

16 Claims, 5 Drawing Sheets

(51) Int. Cl.
  *A46B 13/00* (2006.01)
  *A46B 13/02* (2006.01)
  *A61B 90/80* (2016.01)

(56) References Cited

U.S. PATENT DOCUMENTS

| | | | |
|---|---|---|---|
| 6,401,289 B1 | 6/2002 | Herbert | |
| 6,523,214 B1 | 2/2003 | Kaiser | |
| 6,569,170 B1 | 5/2003 | Kellogg | |
| 6,575,924 B2 | 6/2003 | Wevers et al. | |
| D500,854 S | 1/2005 | Eichel | |
| D510,138 S | 9/2005 | Kim | |
| 7,116,018 B2 | 10/2006 | Strobl | |
| D533,943 S | 12/2006 | Chen | |
| D548,341 S | 8/2007 | Ohta et al. | |
| D549,964 S | 9/2007 | Roth et al. | |
| 7,320,691 B2 * | 1/2008 | Pilcher | A61B 17/54 604/289 |
| D573,346 S | 7/2008 | Daubenspeck et al. | |
| D601,803 S | 10/2009 | Reishus et al. | |
| 7,786,626 B2 | 8/2010 | Reishus et al. | |
| 7,789,092 B2 | 9/2010 | Akridge et al. | |
| D646,487 S | 10/2011 | Leppla et al. | |
| D648,435 S | 11/2011 | Brodbeck | |
| D675,829 S | 2/2013 | Jakubow | |
| D679,502 S | 4/2013 | Itano et al. | |
| D683,139 S | 5/2013 | Chikos et al. | |
| 2003/0032900 A1 | 2/2003 | Ella | |
| 2003/0127918 A1 | 7/2003 | Fukunaga et al. | |
| 2003/0163068 A1 | 8/2003 | Kang | |
| 2004/0039403 A1* | 2/2004 | Glucksman | A45D 26/0061 606/133 |
| 2005/0143754 A1* | 6/2005 | Zelickson | A61B 17/54 606/131 |
| 2005/0278877 A1 | 12/2005 | Akridge et al. | |
| 2008/0104787 A1 | 5/2008 | Keenan et al. | |
| 2008/0106156 A1 | 5/2008 | Reishus et al. | |
| 2009/0234304 A1 | 9/2009 | Zelickson et al. | |
| 2010/0281636 A1* | 11/2010 | Ortins | A46B 9/04 15/4 |
| 2011/0160814 A2 | 6/2011 | Tucker et al. | |
| 2012/0016239 A1 | 1/2012 | Barthe et al. | |
| 2012/0165710 A1 | 6/2012 | Nichols | |
| 2012/0296342 A1* | 11/2012 | Haglund Wendelschafer | 606/131 |
| 2013/0046212 A1 | 2/2013 | Nichols | |

* cited by examiner

SKIN TREATMENT APPARATUS

BACKGROUND

Technical Field

The present disclosure relates to a skin treatment apparatus, and, in particular, relates to a facial brush or cleanser apparatus having cyclic treatment capabilities with visual icons or indicia to assist the user in operation and use of the apparatus.

Facial brush devices for cleaning and/or facial massage are known in the art. These devices typically incorporate a head having bristles, which vibrate or oscillate during activation to engage the skin and apply a cleanser, to exfoliate, to massage etc. An example of a facial brush is the commercially available Power Facial Cleanser, Model 3710, manufactured by CONAIR of Stamford, Conn., which is a battery-operated, two speed cleaning system.

SUMMARY

Accordingly, the present disclosure is directed to further improvements in facial brush apparatuses, particularly, handheld facial brushes, massagers or cleaners. In accordance with one embodiment, a facial treatment apparatus includes a housing, a facial treatment member mounted to the housing, and dimensioned for application to facial skin of a subject and being actuable to treat the facial skin, a visual display including a facial icon having a plurality of regions corresponding to different areas of the facial skin to be treated by the facial treatment member, a timer adapted to count time associated with a treatment protocol and responsive to actuation of the facial treatment member and a controller associated with the timer and the facial icon and cooperating to visually identify a different region of the facial icon at successive predetermined time intervals of the treatment protocol.

The visual display may include a time indicator associated with the timer and adapted to identify time associated with the treatment protocol. In one embodiment, the time indicator is adapted to display time remaining in the treatment protocol.

The visual display may include a mode indicator for indicating a mode of the treatment protocol corresponding to a select predetermined time interval of the treatment protocol. The treatment protocol may include at least three different predetermined time intervals corresponding to at least three modes of the treatment protocol. In embodiments, the treatment protocol may include six different predetermined time intervals corresponding to six modes of the treatment protocol. Each of the predetermined time intervals of the modes may be substantially equal.

A manual actuator is mounted to the housing and in electrical communication with a motor for actuating the facial treatment member. The manual actuator is activated to selectively control operation of the motor between two different speeds.

In another embodiment, a facial treatment apparatus includes a housing, a facial treatment member mounted to the housing, and dimensioned for application to facial skin of a subject, and being actuable to treat the facial skin, a visual display including a facial icon mounted to the housing and having first and second regions corresponding to respective first and second areas of the facial skin to be treated by the facial treatment member, a timer adapted to count time associated with a treatment protocol and responsive to actuation of the facial treatment member, and a controller associated with the timer and the facial icon and cooperating to visually identify the first and second regions of the facial icon during respective first and second modes of the treatment protocol. The visual display further may include a mode indicator adapted to respectively display the first and second modes of the treatment protocol. The visual display further may include a time indicator adapted to display time associated with the treatment protocol.

The facial treatment apparatus of the present disclosure includes a visual display, which enhances functionality of the apparatus by guiding the user in treating select regions of the face for predetermined time intervals. Moreover, the treatment apparatus automatically changes between modes of a treatment protocol to ensure the user treats the entire facial area. Time associated with the treatment protocol and the operational status of the treatment element is displayed by the visual display.

Other advantages of the present invention are detailed hereinbelow.

BRIEF DESCRIPTION OF THE DRAWINGS

Embodiment(s) of the present disclosure will be more readily appreciated by reference to the drawings wherein.

DETAILED DESCRIPTION OF THE PREFERRED EMBODIMENTS

Referring now to FIGS. 1-4, the facial treatment apparatus 10 in accordance with the principles of the present disclosure is illustrated. The facial treatment apparatus 10 includes a base 12 and a handheld member 14 which is mountable to the base 12. The base 12 may reside on a support surface and defines a receptacle 16 for reception of the end of the handheld member 14. The base 12 may include a charging unit with electrical contacts for charging the handheld member, and may be connected to a standard A/C outlet through an electric cord 18.

The handheld member 14 includes an outer housing or frame 20 and a facial treatment element 22 mounted to one end of the frame 20. The other end of the frame 20 opposing the facial treatment element 22 is dimensioned for reception within the receptacle 16 of the base 14, and may include electrical contacts for coupling with the electrical contacts of the base 12. The handheld member 14 may include a manual actuator 24 in the form of a button or switch for activating the facial treatment element 22.

The facial treatment element 22 may include a plurality of bristles 26 which may move relative to the frame 20. In one embodiment, the bristles 26 are adapted to oscillate, e.g., concurrently, and may be mounted to a single plate or disc within the frame 20. The single plate or disc may be translated or reciprocated by an internal motor. In other embodiments, the bristles 26 may be adapted to rotate. Alternatively, the facial treatment element 22 may be a foam or cloth pad, which may oscillate, rotate or vibrate. The facial treatment element 22 may be releasably couplable to the frame 20 to permit interchanging of other facial treatment elements 22.

Figure 1:
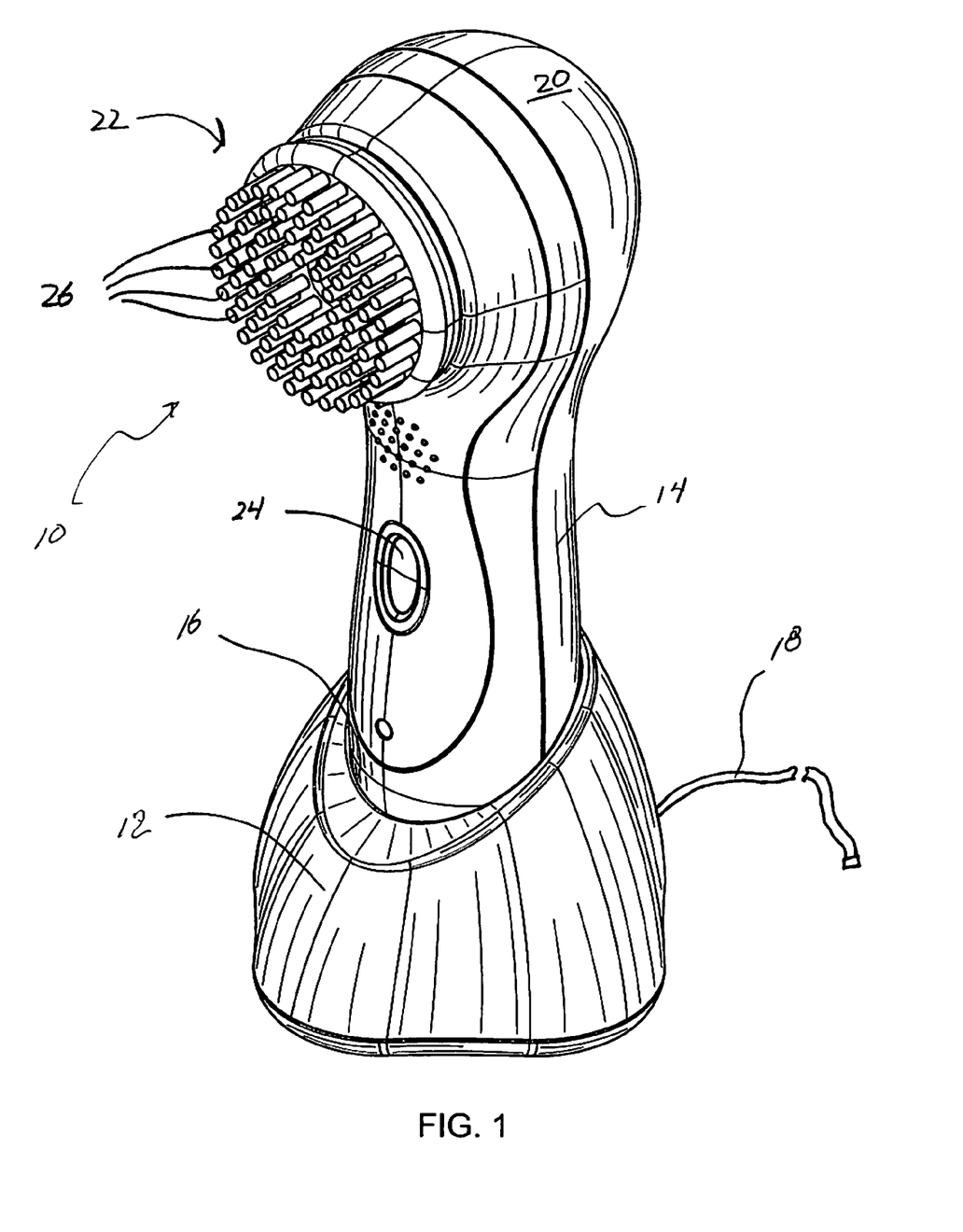
FIG. 1 is a perspective view of the facial treatment apparatus in accordance with the principles of the present disclosure illustrating the base and the handheld member mounted to the base.
Figures 2, 4:
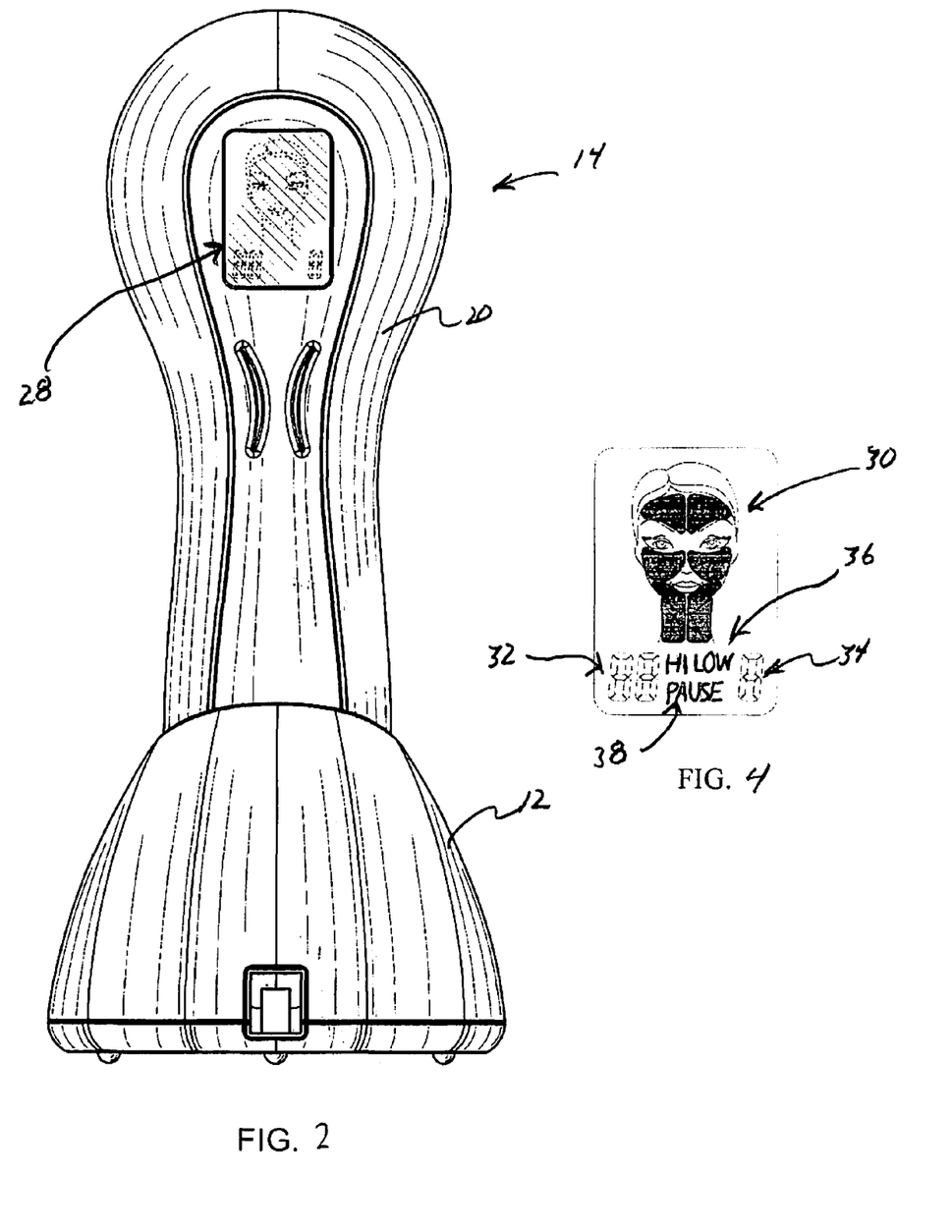
FIG. 2 is a rear elevation view of the facial treatment apparatus.
FIG. 4 is an enlarged view of the visual display of the facial treatment apparatus.
Figure 3:
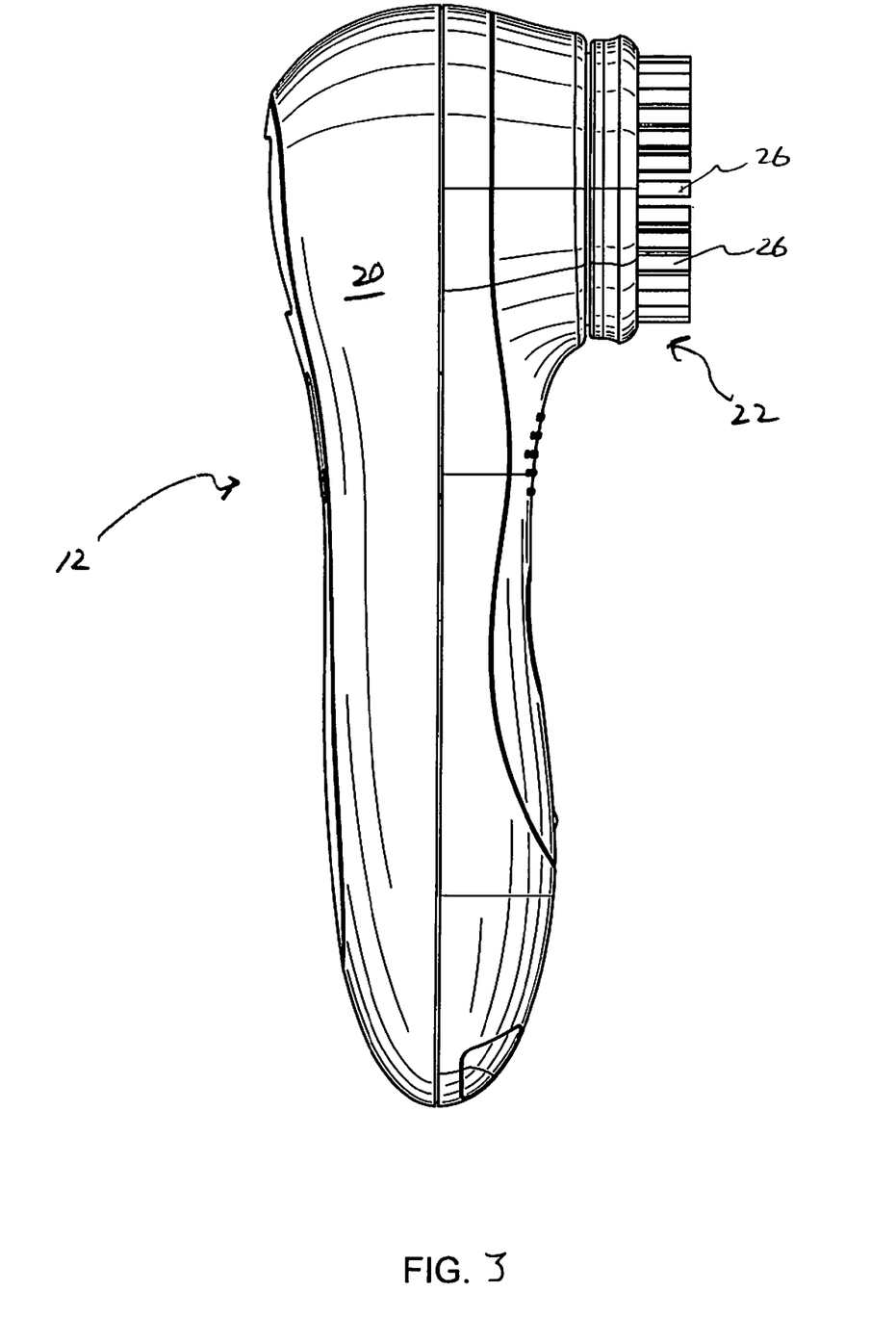
FIG. 3 is a side elevation view of the handheld member of the facial treatment apparatus.

As best depicted in FIGS. 2 and 4, the frame 20 further includes a visual display 28 disposed on the rear of the frame 20, e.g. on the opposed side of the facial treatment element 22. The visual display 28 may include an LCD or other suitable illumination means. The visual display 28 may include three primary components, namely a facial icon 30, a time indicator 32 and a mode indicator 34. The facial icon 30 is representative of the face of a user, and may be in the form of e.g., a head or face of a woman. The facial icon 30 may include at least two regions, which correspond to areas of the face to be treated in accordance with a treatment protocol of the facial treatment apparatus 10—as will be discussed in greater detail hereinbelow. In one embodiment, the facial icon 30 includes six (6) regions. The timer indicator 32 and the mode indicator 34 include numeric characters and represent time remaining in the treatment protocol and the particular mode of treatment, respectively. The visual display 28 also may include a motor status indicator 36 which identifies operating speed (e.g., hi vs. low) and pause indicator 38 of the facial treatment element 22.

The facial icon 30, timer indicator 32 and the mode indicator 34 of the visual display 28 may be illuminated, highlighted and/or darkened via the LCD to identify to the user the respective operational states of these components. Although the visual display 28 is described as being incorporated within the frame 20 of the handheld member 14, in the alternative, the visual display 28 may be incorporated within the base 12 of the facial treatment apparatus 10.

Figure 5:
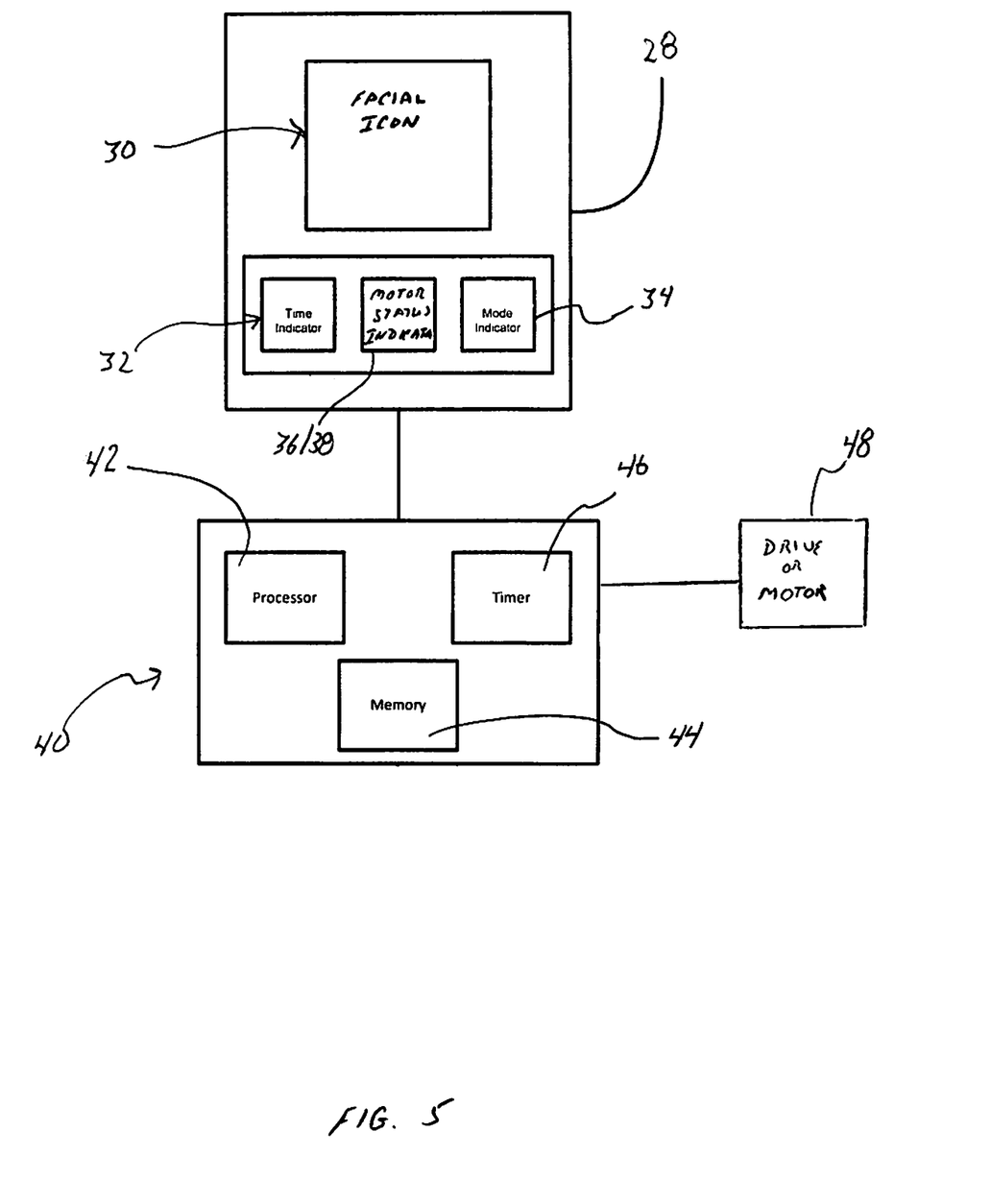
FIG. 5 is a flow diagram illustrating functioning components of the facial treatment apparatus.

Referring now to FIG. 5, further details of the operating components of the facial treatment apparatus 10 will be discussed. The facial treatment apparatus 10 utilizes one or more controllers 40 to receive various information and transform the received information to generate an output. The controller 40 may include any type of computing device, computational circuit, software, logic or any type of processor or processing circuit 42 capable of executing a series of instructions that are stored in a memory. The controller 40 may include multiple processors 42 and/or multicore central processing units (CPUs) and may include any type of processor, such as a microprocessor, digital signal processor, microcontroller, or the like. The controller 40 may also include a memory 44 to store data and/or algorithms to perform a series of instructions. The memory 44 may include a mechanism that provides (e.g., stores and/or transmits) information in a form readable by a machine such as a processor, computer, or a digital processing device. The controller 40 further includes a timer 46, e.g., an electronic timer, which times a sequence of a treatment protocol.

The controller 40 controls operation of the motor or drive 48 of the handheld member 14 to activate/deactivate the facial treatment element 22 and to control functioning of the visual display 28 in accordance with a predefined treatment protocol.

Figure 6A:
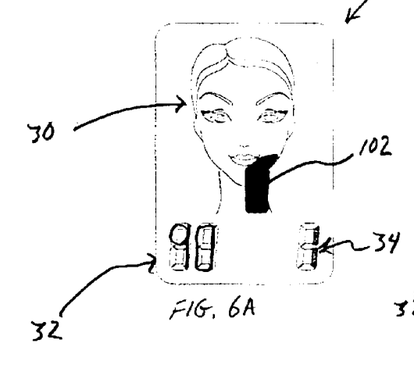
FIGS. 6A-6F are views of the visual display during a treatment protocol of the facial treatment apparatus.

Referring now to FIGS. 4, 5 and 6A-6F, the treatment protocol 100 of the facial treatment apparatus 10 will be described. FIG. 4 illustrates the visual display 28 in an inactive or charging mode, e.g., when the handheld member 14 is positioned properly within the base 12. To initiate the treatment protocol 100, the handheld member 14 is removed from the base 12, and the manual actuator 24 is activated via manual manipulation, e.g., through depression or sliding of the actuator 24. A signal is sent to the controller 40, which, in turn activates the LCD of the visual display 28. FIG. 6A depicts the first mode of operation in accordance with the treatment protocol. In the first mode, the first section or region 102 of the facial icon 30 is activated or illuminated thereby instructing the user to apply the facial treatment element 22 to the corresponding region of the user's face. In the first mode, the mode indicator 34 displays the number 1 and the total treatment time is depicted in the timer indicator 32. In one embodiment, the total treatment time is ninety (90) seconds, and the number "90" appears in the timer indicator 32. The facial treatment apparatus 10 runs in the first mode for a predetermined time interval, which, in one embodiment is fifteen (15) seconds. Thus, the timer 46 of the controller 40 will count down from ninety (90) seconds to seventy-five (76) seconds and display the corresponding time remaining in the treatment protocol on the timer indicator 32.

Figure 6B:
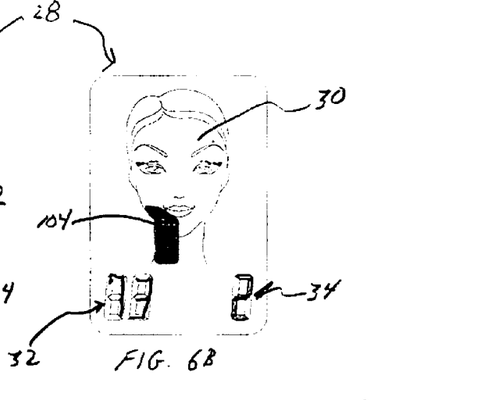

FIG. 6B illustrates the second mode of operation. The second mode of operation is automatically activated upon finishing the first mode, e.g., upon elapsing of fifteen (15) seconds of the predetermined time interval. In the second mode, the second section or region 104 of the facial icon 30 is illuminated, darkened or highlighted thereby instructing the user to apply the facial treatment element 22 to the corresponding region of the user's face. Upon initiating the second mode, the number 2 is displayed by the mode indicator 34 and the time remaining of the total treatment time is displayed, e.g., seventy-five (75) seconds, in the timer indicator 32. The timer indicator 32 incrementally displays the numbers "75" to "61" representative of the time remaining in the treatment protocol.

Figure 6C:
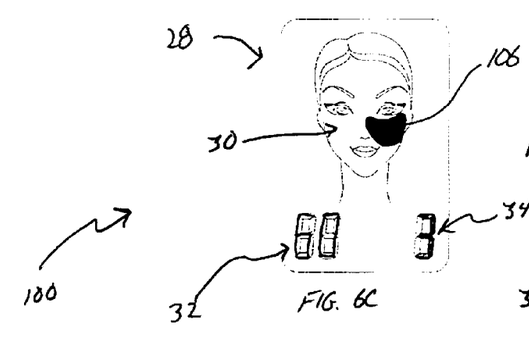

FIG. 6C depicts the third mode of operation, which is automatically activated upon elapsing of the predetermined time interval of the second mode, e.g., fifteen (15) seconds. In the third mode, the third region 106 of the facial icon 30 is highlighted thereby instructing the user to apply the facial treatment element 22 to the corresponding region of the user's face, and the mode indicator 34 displays the number 3. The time remaining of the total treatment time is displayed, e.g., sixty (60) seconds, in the timer indicator 32. The timer indicator 32 incrementally displays the numbers "60" to "46" representative of the time remaining in the treatment protocol.

Figure 6D:
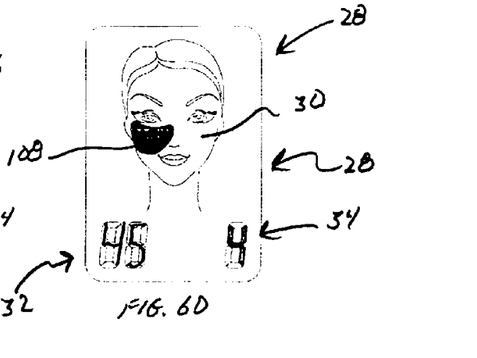
Figure 6E:
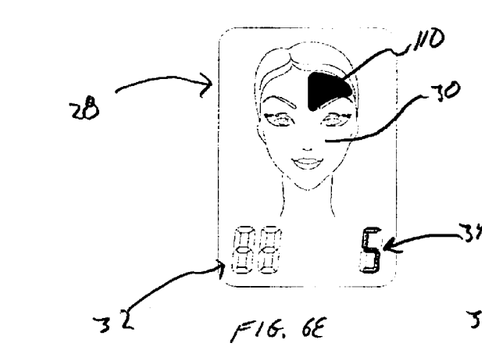
Figure 6F:
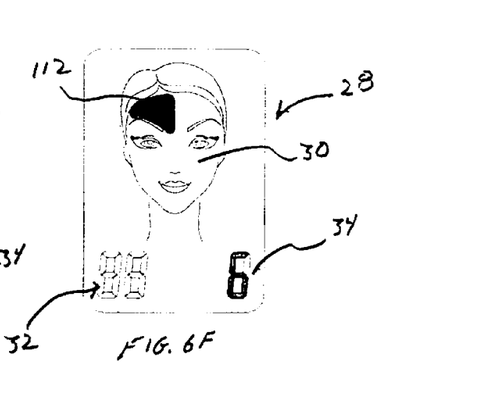

FIG. 6D illustrates the fourth mode of operation where the fourth region 108 of the facial icon 30 is darkened, the number 4 displayed in the mode indicator 34 and the time remaining in the treatment protocol is displayed in the timer indicator 32, e.g., forty-five (45) seconds. Upon elapsing of the predetermined time interval, e.g., fifteen (15) seconds, the fifth mode of the treatment protocol is activated (FIG. 6E) where the fifth region 110 of the facial icon 30 is highlighted or darkened, the number 5 displayed in the mode indicator 34 and the time remaining in the treatment protocol is displayed in the timer indicator 32, e.g., thirty (30) seconds. FIG. 6F depicts the sixth mode of operation, which is activated upon completion of the fifth mode. In the sixth mode, the sixth region 112 of the facial icon 30 is darkened, the number 6 displayed in the mode indicator 34 and the time remaining in the treatment protocol is displayed in the timer indicator 32, e.g., forty-five (15) seconds. The timer indicator 32 incrementally displays the numbers "15" to "1" representative of the time remaining in the treatment protocol in the sixth mode. At the end of the sixth mode, the visual display 28 and the motor 48 are deactivated.

During operation of the apparatus 10, the motor 48 may be switched between two different speeds by pressing or actuating the manual actuator 24. For example, upon initial actuation, depression of the manual actuator 24 will initiate the motor 48 and the facial treatment element 22 at a high speed, which will cause the "HI" indicia (FIG. 4) of the motor status 36 to be darkened or highlighted. If the manual actuator 24 is depressed again, the motor 24 and the facial treatment element 22 will operate at a lower speed as controlled via the controller 40 and the "LOW" indicia will be highlighted or darkened within the motor status indicator 36 of the visual display 28. In certain embodiments, if the manual actuator 24 is depressed again when in the "LOW" mode, the motor 48 and the timer 32 will pause, and the pause indicator "PAUSE" or icon 38 will be highlighted. In the "PAUSE" mode, the visual display 28 may remain activated displaying the mode, the facial region associated with the mode and the time remaining in the treatment protocol. Depressing or actuating the manual actuator 24 again may continue the treatment, when in the "PAUSE" mode, which will initiate the motor 48 and the facial treatment at "HI" speed. In embodiments, if the treatment apparatus 10 is left in the "PAUSE" mode for a predetermined time period, e.g., two (2) minutes, the apparatus 10 will be deactivated and the treatment protocol will be reset. In some embodiments, if the manual actuator 24 is depressed for a period, e.g., one (1) second, the apparatus 10 will be deactivated and the treatment protocol reset.

It is also envisioned that upon completion of each mode, the motor 48 and the timer 32 may pause for a predefined period of time, e.g., about 0.5 seconds, before initiating the next successive mode. Other alternatives are also envisioned. For example, the time interval for each mode may be the same or different, and may be for periods longer or shorter than described hereinabove. The time indicator 32 may display time remaining in each mode as opposed to time remaining in the treatment protocol. The regions of the face displayed by the facial icon may be more or less than six regions.

The treatment apparatus 10 may be used in conjunction with a cleaner, skin conditioner or ointment, as a massager, as an exfoliating device and/or include any treatment of the face. The treatment apparatus 10 may be adapted for use with other body regions whereby the visual display may incorporate an icon representative of any other body region.

The above description and the drawings are provided for the purpose of describing embodiments of the present disclosure and are not intended to limit the scope of the disclosure in any way. It will be apparent to those skilled in the art that various modifications and variations can be made without departing from the spirit or scope of the disclosure. Thus, it is intended that the present disclosure cover the modifications and variations of this disclosure provided they come within the scope of the appended claims and their equivalents.

What is claimed is:

1. A facial treatment apparatus, which comprises:
   a housing;
   a facial treatment member mounted to the housing, the treatment member dimensioned for application to facial skin of a subject and being actuatable to treat the facial skin;
   a visual display including a facial icon having a plurality of regions corresponding to different areas of the facial skin to be treated by the facial treatment member, each of the plurality of regions being associated with a corresponding mode of a treatment protocol;
   a timer adapted to count time associated with the treatment protocol and responsive to actuation of the facial treatment member, the treatment protocol including six different predetermined time intervals corresponding to six modes of the treatment protocol and to different regions of the facial icon; and
   a controller including a processor and a memory and configured to illuminate a specific region of the facial icon at successive predetermined time intervals of the treatment protocol based on the time counted by the timer to instruct the subject to apply the facial treatment member for a predetermined time interval to an area of the facial skin corresponding to the illuminated specific region of the facial icon and activate the mode of the treatment protocol associated with the illuminated specific region of the facial icon.

2. The facial treatment apparatus according to claim 1 wherein the visual display includes a time indicator associated with the timer, and adapted to identify time associated with the treatment protocol.

3. The facial treatment apparatus according to claim 2 wherein the time indicator is adapted to display time remaining in the treatment protocol.

4. The facial treatment apparatus according to claim 2, further comprising a mode indicator for indicating the mode of the treatment protocol corresponding to a select predetermined time interval of the treatment protocol.

5. The facial treatment apparatus according to claim 1 wherein each of the predetermined time intervals are substantially equal.

6. The facial treatment apparatus according to claim 1 wherein the facial icon is representative of a face.

7. The facial treatment apparatus according to claim 1, further comprising a manual actuator mounted to the housing and a motor in electrical communication with the manual actuator for actuating the facial treatment member.

8. The facial treatment apparatus according to claim 7 wherein the manual actuator is activated to selectively control operation of the motor between two different operating speeds to cause corresponding respective movement of the facial treatment member.

9. A facial treatment apparatus, which comprises:
   a housing;
   a facial treatment member mounted to the housing;
   a visual display including a facial icon mounted to the housing, the facial icon having six regions each corresponding to a respective area of the facial skin to be treated by the facial treatment member, each of the six regions being associated with a different mode of a treatment protocol;
   an electronic timer adapted to count time associated with each of the modes of the treatment protocol, the treatment protocol including six different predetermined time intervals corresponding to six modes of the treatment protocol and to six regions of the facial icon; and
   a controller including a processor and a memory and configured to illuminate the six regions of the facial icon during respective modes of the treatment protocol based on the time counted by the electronic timer to instruct a user to apply the facial treatment member to the respective one of the six areas of the facial skin during the respective mode of the treatment protocol.

10. The facial treatment apparatus according to claim 9 wherein the visual display includes a mode indicator adapted to respectively display the six modes of the treatment protocol.

11. The facial treatment apparatus according to claim 9 wherein the visual display includes a time indicator adapted to display time associated with the treatment protocol.

12. The facial treatment apparatus according to claim 11 wherein the time indicator is adapted to display time remaining in the treatment protocol.

13. The facial treatment apparatus according to claim 1 wherein the visual display is mounted to the housing.

14. The facial treatment apparatus according to claim 8 wherein the controller is in communication with the manual actuator and includes logic such that successive actuation of the manual actuator will cause the motor to selectively operate between a high speed mode, a low speed mode and a pause mode.

15. The facial treatment apparatus according to claim 9, further comprising a manual actuator mounted to the housing and a motor in electrical communication with the manual actuator for moving the facial treatment member.

16. The facial treatment apparatus according to claim 15 wherein the controller is in communication with the manual actuator and includes logic such that successive actuation of the manual actuator will cause the motor to selectively operate between a high speed mode, a low speed mode and a pause mode.

\* \* \* \* \*